US012584913B2

(12) United States Patent
Lei et al.

(10) Patent No.: US 12,584,913 B2
(45) Date of Patent: Mar. 24, 2026

(54) DEVICE FOR DETECTING AN ANALTE IN A LIQUID SAMPLE

(71) Applicant: Zhejiang Orient Gene Biotech Co., Ltd, Huzhou (CN)

(72) Inventors: Siyu Lei, Huzhou (CN); Jianqiu Fang, Huzhou (CN)

(73) Assignee: ZHEJIANG ORIENT GENE BIOTECH CO., LTD., Zhejiang (CN)

( * ) Notice: Subject to any disclaimer, the term of this patent is extended or adjusted under 35 U.S.C. 154(b) by 677 days.

(21) Appl. No.: 17/868,370

(22) Filed: Jul. 19, 2022

(65) Prior Publication Data

US 2023/0296598 A1 Sep. 21, 2023

Related U.S. Application Data

(60) Provisional application No. 63/333,299, filed on Apr. 21, 2022, provisional application No. 63/327,048, filed on Apr. 4, 2022.

(30) Foreign Application Priority Data

Mar. 15, 2022 (CN) .......................... 202210254433.4
Apr. 11, 2022 (CN) .......................... 202210377142.4

(51) Int. Cl.
| | |
|---|---|
| G01N 33/543 | (2006.01) |
| A61B 10/00 | (2006.01) |
| B01L 3/00 | (2006.01) |
| B01L 9/00 | (2006.01) |
| G01N 1/10 | (2006.01) |
| G01N 33/569 | (2006.01) |

(52) U.S. Cl.
CPC ... *G01N 33/54388* (2021.08); *A61B 10/0051* (2013.01); *A61B 10/0096* (2013.01); *B01L 3/5023* (2013.01); *B01L 3/5029* (2013.01); *B01L 9/00* (2013.01); *G01N 1/10* (2013.01); *G01N 33/56983* (2013.01); *B01L 2300/0825* (2013.01); *B01L 2400/0406* (2013.01); *G01N 2001/1056* (2013.01); *G01N 2333/165* (2013.01)

(58) Field of Classification Search
None
See application file for complete search history.

(56) References Cited

U.S. PATENT DOCUMENTS

| | | | |
|---|---|---|---|
| 5,352,410 A | 10/1994 | Hansen et al. | |
| 5,376,337 A | 12/1994 | Seymour | |
| 5,576,009 A | 11/1996 | Nastke et al. | |
| 2006/0292036 A1* | 12/2006 | Gould | B01L 3/5029 |
| | | | 422/400 |
| 2010/0172797 A1 | 7/2010 | Gould et al. | |
| 2021/0402398 A1* | 12/2021 | Rothberg | B01L 3/5023 |

FOREIGN PATENT DOCUMENTS

JP 2010-271040 A 12/2010

* cited by examiner

*Primary Examiner* — Matthew D Krcha
(74) *Attorney, Agent, or Firm* — MUNCY, GEISSLER, OLDS & LOWE, P.C.

(57) ABSTRACT
The present invention provides a device for detecting an analyte in a sample, including a chamber for receiving a testing element, where the testing element has a first position and a second position in the chamber; the testing element is not in contact with a fluid sample when the testing element is located in the first position, and the testing element is in contact with a fluid sample when the testing element is located in the second position.

17 Claims, 14 Drawing Sheets

DEVICE FOR DETECTING AN ANALTE IN A LIQUID SAMPLE

CROSS-REFERENCE TO RELATED APPLICATIONS

The present application claims priority to a Chinese prior application No. 2022103771424 and filed on Apr. 11, 2022, a Chinese prior application No. 2022102544334 and filed on Mar. 15, 2022, as well as a US prior provisional application No. 63/333,299 and filed on Apr. 21, 2022, and a US prior provisional application No. 63/327,048 and filed on Apr. 4, 2022; the entire contents of the above application, including the description, accompanying drawings and claims of which are incorporated herein as a portion of the present invention.

TECHNICAL FIELD

The present invention relates to a device for collecting and detecting a liquid sample, in particular, a device for collecting and detecting an analyte in a liquid sample in the field of rapid diagnosis, such as a urine and saliva collection and detecting device.

BACKGROUND

The following description is merely an introduction to the background art and not to limit the present invention.

At present, the test device for detecting the presence or absence of an analyte in sample is widely used in hospitals or homes, and such device for rapid diagnosis comprises one or more test strips, such as early pregnancy detection, drug abuse detection, etc. The apparatus is very convenient, and the detection result can be obtained from the test strip after one minute or no more than ten minutes.

The drug detection is widely used by drug control department, Public Security Bureau, drug rehabilitation centers, physical examination centers, the national conscription offices, etc. The drug detection is diverse and frequent. Some detections need to collect samples and then samples are detected in professional testing agency or testing laboratories, and some detections needs to be completed in the site in time, for example, roadsides, for example, persons who drive after drug use need to be tested on the spot (referred to as "Drug Driving"), to obtain the results in time. For example, the detection of saliva samples is gradually accepted and favored by testing agencies or testing personnel due to convenient collection. In some literatures, various sample collection and detecting devices for clinical and domestic uses have been described. For example, the U.S. Pat. No. 5,376,337 discloses a saliva sampling device in which a piece of filter paper is used to collect saliva from the mouth of a subject and deliver saliva to an indicator reagent. The U.S. Pat. Nos. 5,576,009 and 5,352,410 have disclosed a syringe-type fluid sampling device.

Moreover, with the transmission of infectious diseases in recent years, in particular to corona virus, household self-inspection has become mainstream products. Household self-inspection is convenient for sampling and friendly in operation, and can prevent the contamination to the environment due to sampling. It is more demanding for household self-inspection products.

In view of the above technical problems in some conventional products, it is necessary to improve them and provide an alternative approach to solve the drawbacks of the prior art, thus satisfying the ever-increasing demands for in vitro diagnosis, in particular to the demands for the household self-inspection market.

SUMMARY

Directed to the above situation, to overcome the shortcomings in the prior art, the objective of the present invention is to provide a device for detecting an analyte in a fluid sample, and a receiving device which is matched with the detecting device and used for receiving the detecting device. The receiving device includes a chamber, and the chamber includes a liquid chamber for holding a liquid and an inserting chamber for a testing element to insert. The "receiving" in the receiving device is not construed as limiting the specific purpose of the device; the receiving device may be called a liquid treatment and mixing device, and also may be called a liquid sample conveying and transferring device and thus, may be called a device.

A first aspect of the present invention provides a device for detecting an analyte, including a chamber for receiving a testing element, where the testing element has a first position and a second position in the chamber; the testing element is not in contact with a fluid sample when the testing element is located in the first position, and the testing element is in contact with a fluid sample when the testing element is located in the second position.

In some detailed embodiments, the chamber for receiving the testing element is further provided with a collector for collecting a fluid sample collector, and the collector is disposed on one end of the chamber. In some embodiments, the sample collector may be in dectable combination with the chamber. In some embodiments, the sample collector is a sponge swab or flocking swab for collecting the fluid sample. In some embodiments, the sample collected by the collector may not or will not flow onto the testing element. In some embodiments, the collector is treated, mixed or eluted by a solution located in the chamber; a portion of the testing element is allowed to enter the receiving device to contact liquid, thereby completing the detection. In some embodiments, the portion of the testing element includes sample receiving are or a sample application cushion of the testing element.

In some embodiments, the chamber for receiving the testing element further includes a carrier used for bearing the testing element; the carrier has a first position and a second position in the chamber; and the carrier drives the testing element to change or move between the first position and the second position.

In some preferred embodiments, the device further includes a sliding element, and the sliding element is connected to the chamber for receiving the testing element via a locking structure. The term "connect" herein refers to the connection in a relatively fixed position; in case of being in a locking state, the sliding element is fixed on a relatively fixed position of the chamber; in case of being unlocked state, the sliding element may move or slide on the chamber. The way of sliding refers to sliding from the first position to the second position. In some embodiments, the sliding element is connected with the carrier; when the sliding element is located in a locking position, the carrier may not move relative to the chamber for receiving the testing element. In some other embodiments, when the locking structure is unlocked, the sliding element may move relative to the chamber for receiving the testing element, thus driving the carrier to move. In some embodiments, when the carrier is located in the first position, the carrier is fixed on or in the chamber for receiving the testing element by the locking structure; after being unlocked, the carrier is allowed to move from the first position to the second position by moving the locking structure. In some embodiments, when the carrier is located in the first position, the sliding element is fixed on or in the chamber for receiving the testing element by the locking structure; after being unlocked, the carrier is allowed to move from the first position to the second position by moving the sliding element.

In some embodiments, when the carrier is located in the first position, the testing element on the carrier is not in contact with a fluid sample; when the carrier is located in a second position, the carrier is in contact with a fluid sample such that the testing element is in contact with the fluid sample. In this way, the fluid sample flows on the testing element such that the test result may be read out on the testing area of the testing element.

In some embodiments, the locking structure includes one or more bolt structures; the chamber for receiving the testing element includes one or more notched structures for receiving the bolt; the bolt is inserted into the notch to be fixed or locked in a locking state. In some embodiments, the sliding element is provided with a bolt having a locking structure; the chamber for receiving the testing element has a notch for receiving the bolt. The sliding element is located in the first position with the chamber via the locking structure, and after being unlocked, the sliding element may slide relative to the chamber.

In some embodiments, the sliding element includes a connecting piece integrally connected with the carrier and a portion of the locking structure. In some embodiments, the sliding piece of the locking structure may slide on a sliding groove of the chamber. In some embodiments, the sliding may drive the carrier to slide or move from the first position to the second position.

The so-called "locking structure" includes at least two functions, namely, a locking function and unlocking function. The locking function may directly or indirectly enable the carrier to be fixed relative to the chamber for receiving the testing element. After being unlocked, the carrier is directly or indirectly allowed to be not fixed relative to the chamber for receiving the testing element, that is, capable of achieving mutual or relative movement. When there is a sliding element, the sliding element includes a portion of the locking structure; and the chamber for receiving the testing element includes another portion of the locking structure; these two portions are matched to complete the locking state or unlocking state.

In some embodiments, the sliding element includes a bulge structure, and the chamber for receiving the testing element has a notched structure for receiving the bulge; the bulge structure is matched with the notched structure to achieve the functions of the locking structure. In some embodiments, the notched structure is elastic, while the bulge structure is not elastic. The bulge structure and the notched structure form the locking structure of the embodiments of the present invention. When the bulge structure is received by the notched structure, or the bulge structure is meshed or engaged with the notched structure, the sliding element and the chamber for receiving the testing element are in locking state; when the bulge structure is separated from the notched structure, it is in unlocking state. In some embodiments, the chamber for receiving the testing element includes a side wall; the notched structure is located on the chamber and is a portion of the side wall of the chamber. In some embodiments, one end of the notched structure is connected to the side wall of the chamber for receiving the testing element; the other three sides are not connected to the side wall of the chamber for receiving the testing element such that the notched structure has certain elasticity. The "elastic" herein is a relative concept over the bulge structure; the bulge structure presses the notched structure while sliding along the notched structure such that the notched structure is pressed to generate elastic deformation. When the bulge structure enters into the notched structure, the sliding element is locked on the chamber relying on elasticity. Meanwhile, when the sliding element needs to move, the bulge structure is separated from the notched structure such that the sliding element is located in the unlocking state.

In some embodiments, the device further includes a limiting structure such that the sliding distance of the sliding element on the chamber for receiving the testing element is constant. That is, the distance of the sliding element moving from the first locking state to the second position is fixed. In some embodiments, the limiting structure is a sliding groove structure on the chamber for receiving the testing element. In some embodiments, the sliding groove is located on the chamber for receiving the testing element, and a sliding rail is disposed on the testing element. The sliding rail slides on the sliding groove. In some embodiments, the sliding groove structure includes a sliding rail having a bottom surface, or a sliding groove which has no bottom surface and shows an opening penetrating through the side wall. The "receiving" herein represents the function of the chamber, and may represent the testing element owned in the chamber, and also represent the chamber free of the testing element, showing the specific purpose of the chamber.

In some embodiments, the chamber for receiving the testing element includes a limiting structure bulging inward from the side wall. The limiting structure makes the carrier inserted into the chamber via an only direction. The chamber for receiving the testing element is a cylindrical structure; the carrier shows a curved surface or arc-shaped structure, and the carrier has a first surface for bearing the testing element and a second surface in contact with the limiting structure. In some embodiments, the arc-shaped carrier has a groove for accommodating the testing element; the carrier further includes a protection structure for protecting the testing element; and the protection structure is located on the side wall of the groove.

In some embodiments, the side wall of the chamber penetrates through the inside of the sliding element. In some embodiments, the sliding element includes a chamber structure, or called a chamber for sliding; a first sliding rail and a second sliding rail are disposed on the side wall inside the chamber for sliding; the first sliding rail is used for sliding in a sliding groove with a bottom surface; the second sliding rail is used for sliding in a sliding groove penetrating through the side wall of the chamber for receiving the testing element. In some other embodiments, the second sliding rail is used to be connected with the carrier. In this way, the sliding element enables the carrier to move on the chamber via the sliding of the sliding rail on the chamber during sliding. In some embodiments, the chamber for receiving the testing element is divided into a first portion of chamber side wall and a second portion of chamber side wall by the sliding groove having a penetrating opening such that the first portion and second portion of the side wall of the chamber for receiving the testing element are respectively distributed at both sides of the second sliding rail, thus crossing the inside of the chamber for receiving the testing element. In this way, the sliding element may slide outside the chamber for receiving the testing element and drives the carrier in the chamber for receiving the testing element to move in the carrier. In this way, the chamber for receiving the testing element actually penetrates through the sliding element and moves relative to the sliding element. In some embodiments, the movable element includes a first sliding rail and a third sliding rail, a second sliding rail and a fourth sliding rail distributed symmetrically. The first and third sliding rails move in the sliding groove with a bottom surface; the second and fourth sliding rails move in the opening sliding groove of the receiving chamber.

In some embodiments, the testing element on the curved surface carrier includes a testing area and a sample application area in contact with samples. In some embodiments, the testing area is close to one end of the chamber or close to the sliding element; the sample application area is close to another end of the chamber. In some embodiments, another end of the chamber for receiving the testing element is used to be matched with an accommodating chamber or inserted into the accommodating chamber. In this way, when the carrier is moved to the second position from the first position by the sliding element, one end of the carrier is inserted or enters into the accommodating chamber. In this way, the sample application area of the testing element on the carrier is in contact with the liquid in the accommodating chamber, for example, a liquid sample, or a mixture of a treatment solution and a liquid sample, or a fluid sample. Therefore, liquid flows from the sample application area to the testing area by relying on the capillary action of the testing element, thus detecting the presence of an analyte in the sample or not.

In some embodiments, the receiving chamber includes a solution reagent for treating a sample. In some embodiments, the sample collector is allowed to flow into the receiving chamber firstly, and then a portion of the carrier flows into the receiving chamber.

In some embodiments, the apparatus further includes a receiving chamber for receiving the insertion of the collector, and the receiving chamber is independent of a chamber for holding the testing element. In some embodiments, the chamber for receiving the collector may be further used for receiving a portion of the testing element. In some embodiments, the chamber for receiving collector may be further used for receiving a sample application area of the testing element. In some embodiments, the receiving chamber includes a reagent for treating a fluid sample. In some embodiments, the testing element is inserted into or enters into, or has been located in the receiving chamber when the testing element is located in the second position. In some embodiments, a solution reagent is sealed in the receiving chamber in advance. In some embodiments, the sample application area of the testing element is located on the carrier; when the carrier is located in the second position, the sample application area located on the carrier enters into the receiving chamber to be in contact with the fluid sample.

In some embodiments, the carrier may still return to the first position and is fixed on the first position after being located in the second position. When the carrier returns to the first position, test results on the testing element may be read out. Alternatively, when the testing element or carrier is located in the second position, the test result is read out at the testing area. In some embodiments, the chamber for receiving the testing element includes a window used for reading a test result. When the testing element moves to the second position from the first position, the testing area is located under the window.

In some embodiments, the sample is saliva, nasal mucus and throat mucus. In some embodiments, the analyte is virus, bacterium or a drug small molecule.

On the other hand, the present invention provides a method for detecting an analyte in a sample and the method includes:

providing a chamber used for accommodating a testing element; the testing element has a locked first position and an unlocked second position in the chamber; the testing element may be moved to the second position from the first position.

In case of being in the first position, the testing element is not in contact with a fluid sample; in case of being in the second position, the testing element is in contact with a fluid sample.

In some embodiments, the chamber for receiving the testing element further includes a collector for collecting a fluid sample.

In some embodiments, provided is an accommodating chamber, used for combining or linking with the chamber for accommodating the testing element such that the collector is inserted into the accommodating chamber. In some embodiments, the collector is first inserted into the accommodating chamber, and then the testing element moves to the second position from the first position; a portion of the testing element is inserted into or enters to the accommodating chamber, or the sample application area is inserted into or enters to the accommodating chamber. The testing element enters to the accommodating chamber to contact with the sample, thus detecting or testing the analyte.

In some embodiments, the collector is inserted into the accommodating chamber. The treatment solution in the accommodating chamber is in contact with the collector, thus dissolving, lysing and washing the sample on the collector. The sample is mixed with the treatment solution.

In some embodiments, before the collector is inserted into the accommodating chamber, a treatment solution is sealed in the accommodating chamber. In some embodiments, before being inserted into the accommodating chamber, the collector is used to collect a fluid sample, for example, saliva, sweat, blood, urine, sputum or nasal secretion.

In some embodiments, the testing element is locked in the first position and unlocked in the second position such that the testing element moves to the initial first position from the second position and is locked.

In some embodiments, the device further includes a sliding element, and the sliding element drives the testing element to move from the first locking position to the second position. In some embodiments, the testing element is disposed on the carrier and the sliding element drives the carrier to move from the first position to the second position. The sliding element and the chamber for accommodating the testing element have a first locking position and a second position such that the sliding element has a first locking position and a second position in the chamber for accommodating the testing element. In some embodiments, the second position may be or may not be a locking position.

In some embodiments, the sliding element is fixed during the process of moving to the second position from the first position. In some embodiments, the sliding element is sleeved outside the chamber for receiving the testing element; the testing element or the carrier is located in the chamber for receiving the testing element.

In some embodiments, the sliding element includes a locking bolt locked with the chamber for accommodating the testing element, and a sliding rail which slides on the chamber for receiving the testing element; the locking bolt and the chamber or a testing chamber may be in a locking state.

Beneficial Effects

The above structure can be used to achieve the self-detection in a family. The present invention is easy to operate and not prone to making mistakes, and can lower environmental pollution and drop damage to operators.

DETAILED DESCRIPTION OF EMBODIMENTS

Figure 1:
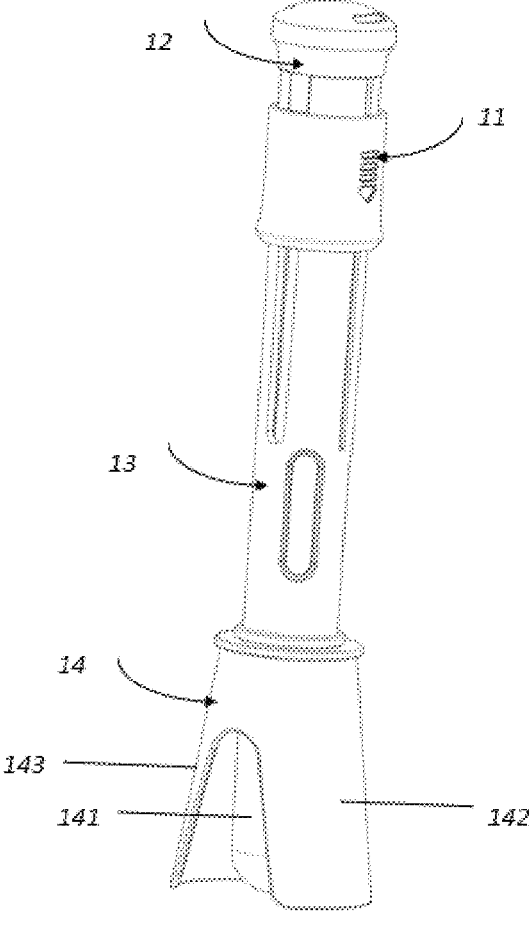
FIG. 1 is a three-dimensional structure diagram showing a package assembly in a detailed embodiment of the present invention (detecting device and accommodating device are assembled)
Figure 2:
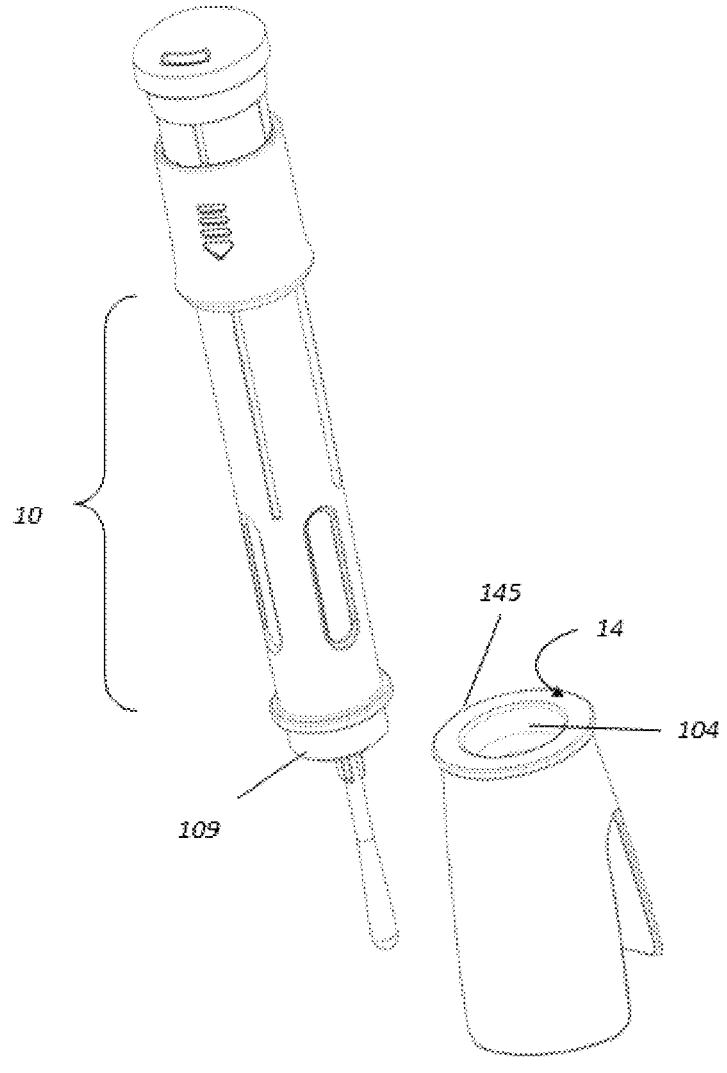
FIG. 2 is a schematic diagram showing a breakdown structure of a testing device in a detailed embodiment of the present invention (detecting device and accommodating device separated)
Figure 3:
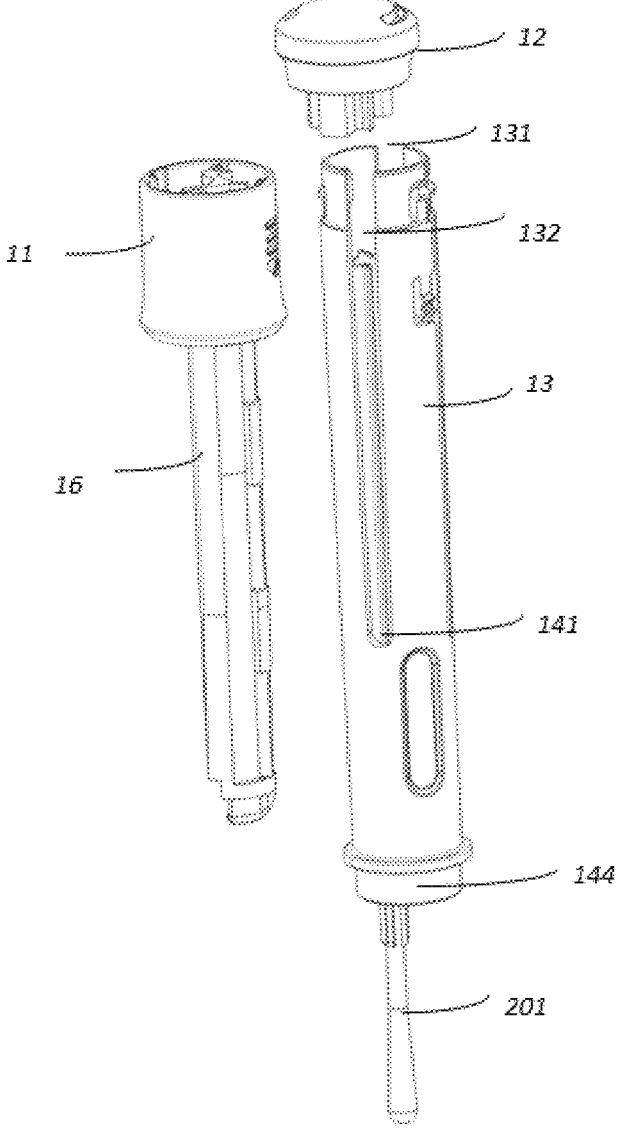
FIG. 3 is a schematic diagram showing a breakdown structure of a detecting device in a detailed embodiment of the present invention.

The structures or technical terms used in the present invention are further described in the following. Unless otherwise indicated, they are understood or interpreted according to ordinary terms and definitions in the art.

Detection

Detection denotes assaying or testing whether a substance or material exists, for example, but not limited to, chemicals, organic compounds, inorganic compounds, metabolites, drugs or drug metabolites, organic tissues or metabolites of organic tissues, nucleic acid, proteins or polymers. Moreover, detection denotes testing the number of a substance or material. Further, assay also denotes immunoassay, chemical detection, enzyme detection and the like.

Samples

The samples that can be detected by the detecting device or collected by the collector of the present invention include biological liquid (e.g. case liquid or clinical samples). Liquid samples or fluid specimens may be derived from solid or semi-solid samples, including excreta, biological tissues and food samples. Solid or semi-solid samples are transformed into liquid samples by any proper method, for example, mixed, mashed, macerated, incubated, dissolved into a proper solution (for example, water, phosphate solution or other buffer solutions), and solid samples are digested by zymolysis. "Biological samples" include samples from animals, plants and food, for example, including urine, saliva, blood and components thereof, spinal fluid, vaginal secretion, semen, faeces, sweat, secreta, tissues, organs, tumors, cultures of tissues and organs, cell culture and medium from human or animals. The preferred biological sample is urine, preferably, the biological sample is saliva, sputum, nasal secretion, and the like. Food samples include substances processed from food, final products, meat, cheese, wine, milk and drinking water. Plant samples are derived from any plants, plant tissues, plant cell cultures and media. "Environmental samples" are derived from the environment (for example, liquid samples, wastewater samples, soil texture samples, underground water, seawater and effluent samples from lakes and other water bodies). Environmental samples may further include sewage or other waste water.

Any analyte can be detected using the appropriate detecting element or testing element of the present invention. Preferably, the present invention is used to detect small drug molecules in saliva and urines. Preferably, the present invention is used to detect virus, bacteria and other small molecules in saliva, throat or nasal cavity fluid. Any form of samples above, either initially solid or liquid, can be collected by the collector 201 in the present invention, as long as the liquid or liquid samples can be absorbed by the absorbing element; and the absorbing element 2022 is generally located on the collector. The absorbing element 2022 here is generally prepared from a water absorbent material and is initially dry. It can absorb liquid or fluid samples by capillary or other characteristics of the absorbing element material, so as to keep the fluid samples in the absorbing element. The absorbent material can be any liquid absorbing material such as sponge, filter paper, polyester fiber, gel, non-woven fabric, cotton, polyester film, yarn, flocking, etc. When a flocking swab is taken, the flocking swab described in the following patents may be used to collect the fluid samples as a part of the present invention: U.S. Pat. Nos. 8,114,027, 8,317,728, 8,979,784, 9,011,358, 9,173,779, 10,327,741, AU2004226798, JP4579902 and ZL200610099310.9. In some embodiments, the absorbing element is hard when it is dry, for example, a sponge becomes soft when it is wet, and can be compressed after softening to release liquid. Of course, when it is a relatively sparse sponge, for example, a sponge swab, liquid samples can be still absorbed in a little amount, for example, 5-100 µL; for example, a sponge swab described in a U.S. provisional application 63/300,811 with application number: Jan.

19, 2022 may be also used in this present invention as a detailed example of the collector.

Of course, the absorbing element is not necessarily prepared by an absorbent material but may be prepared by a non-water absorbent material. But the absorbing element has pores, threads, and cavities, and samples may be collected on these structures. These samples are generally solid or semi-solid samples, and are filled between threads, or in cavities or holes, thus collecting the samples. Of course, optionally, the absorbing element may consist of some non-water absorbent fibers and hairs; these materials are used to scratch solid, semi-solid or liquid samples such that these samples are maintained on the absorbing element.

Downstream and Upstream

Figure 10:
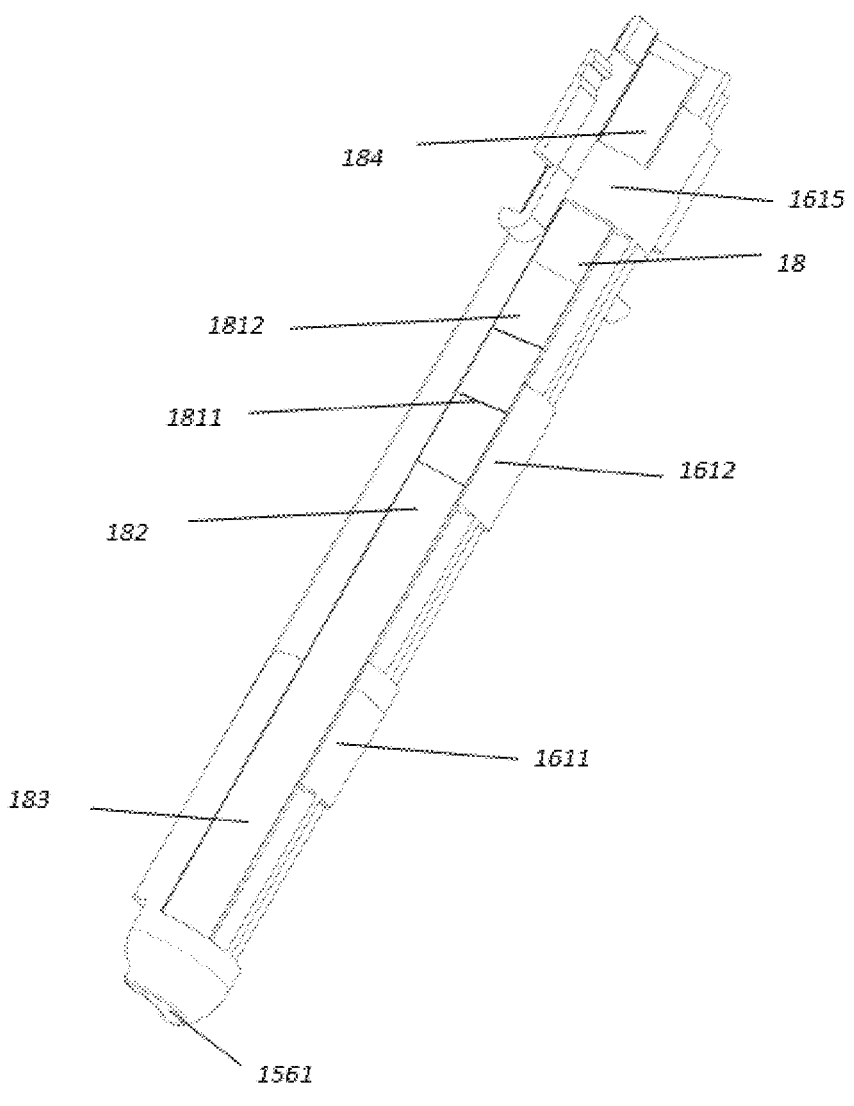
FIG. 10 is a schematic diagram showing a carrier structure in a detailed embodiment of the present invention.

Downstream or upstream is divided according to a flow direction of a liquid, generally, a liquid or fluid flows to a downstream area from an upstream area. The downstream area receives the liquid from the upstream area, and a liquid also may flow to a downstream area along an upstream area. Here, downstream or upstream is generally divided according to a flow direction of a liquid, for example, on some materials where capillary force is utilized to promote the flow of a liquid, a liquid may overcome gravity to flow towards an opposite direction to the gravity; and at this time, downstream or upstream is divided according to a flow direction of the liquid. For example, as shown in FIG. 10, the testing element 18 mentioned herein has a sample application area 183, a labeled area 182, a testing area 181 and an absorption area 184. The sample application area 183 is located upstream of the labeled area 182, and the testing area 181 is located downstream of the labeled area, and the absorption area is located downstream of the testing area. Generally, a fluid flows to the downstream from the upstream along the flow direction of the testing element. In a detailed embodiment of the present invention, when the testing device is vertical, for example, as shown in FIG. 1, a liquid sample will overcome gravity due to capillary force to flow from bottom to top, namely, flowing to the downstream from the upstream once contacts the sample application area 183. In this way, the liquid sample flows through the labeled area 182, and then to the testing area 181, and finally flows to a water absorbing area.

Figure 17:
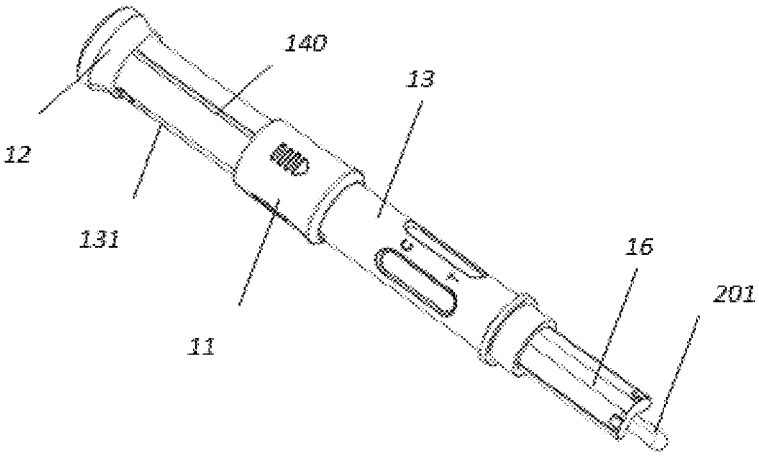
FIG. 17 shows a structure diagram that the sliding element is located in a second position in a detailed embodiment of the present invention.

Of course, the upstream and the upstream here may be also a motion trail or direction of an object instead of a circulation direction of a liquid. For example, in the operating process, after the chamber 14 containing a treatment agent is inserted by an absorber, the chamber is bonded with the chamber with a testing element at this time, as shown in FIG. 1; then the treatment solution in the container contacts the sampling element 201 in the collector to treat the sample. For example, the sample is dissolved, lysed, eluted and the like, and at this time, the testing element located in the chamber is in the initial position. When a sample needs to be detected, it is unlocked such that the testing element 18 or the carrier 16 bearing the testing element can slide within the chamber, thus moving to the second position from the first position. In case of being in the second position, the testing element stretches out from one end of the container chamber 13 (as shown in FIG. 17), for example, stretches out of the chamber with the sample application area into the chamber 101 containing the treatment reagent directly to contact a liquid or a mixture of liquid samples, thus completing the testing or detection.

Gas Flow or Liquid Flow

Gas flow or liquid flow means that liquid or gas can flow from one place to another place. The flow process may pass through some physical structures, to play a guiding role. The "passing through some physical structures" here means that liquid passes through the surface of these physical structures or their internal space and flows to another place passively or actively, where passivity is usually caused by external forces, such as the flow of the capillary action and air pressure action. The flow here may also be a flow due to self-action (gravity or pressure) of the liquid or gas, and also may be a passive flow. The fluid under the action of air pressure may be a forward flow, or also a reverse flow; or a fluid is urged to flow to another position from a position under the action of air pressure. Here, the flow does not mean that a liquid or a gas is necessarily present, but indicates a relationship or state between two objects under some circumstances. In case of presence of liquid, it can flow from one object to another. Here it means the state in which two objects are connected. In contrast, if there exists no gas flow or liquid flow state between two objects, and liquid exists in or above one object but cannot flow into or on another object, it is a non-flow, non-liquid or non-gas flow state.

Detachable Combination

Figure 4:
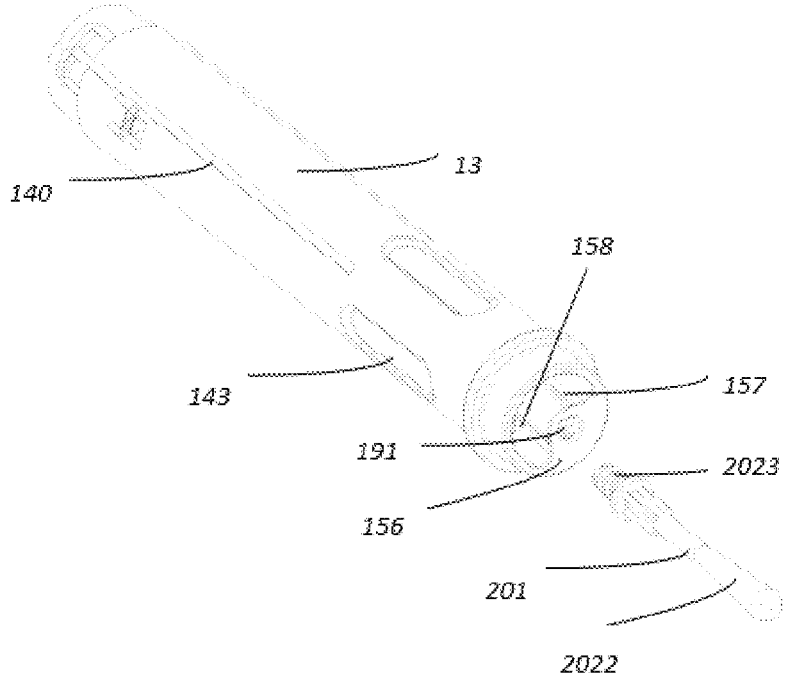
FIG. 4 shows a schematic diagram showing a breakdown structure of a chamber for accommodating the testing element and a collector in a detailed embodiment of the present invention.

A detachable combination means that the connection relationship of two parts is in several different states or locations, for example, when two physical parts are separated initially, they can connect or combine together at an appropriate first condition; and at an appropriate second condition, the two parts can be separated, and the separation is a separation of physical space, without contact. Or, the two parts are combined together initially, and when appropriate, the two parts can be separated physically, or two objects are separated initially, and when required, they combine together to complete some functions, and then separate, or combine again for some purposes subsequently. In a word, the combination or separation of two parts is easy, and such combination or separation can be repeated for many times, of course, it can be one-time combination or separation. In addition, the combination may be a detachable combination between two parts, or a mutually detachable combination between three or more parts, for example, with three parts, the first part is detachably combined with the second part, and the second part can also be detachably combined with the third part, and the first part can also be detachably combined with or separated from the third part. Moreover, the combination between them can be achieved by two detachable objects or indirectly through another object. Here, the absorbing element 201 can be detachably combined with the chamber 13 for accommodating the testing element 18. The detachable combination can be in a direct or an indirect way, as described in details below. The carrier 16 with a testing element is also detachably combined with the chamber 13 of a holding element 18, such that they are combined to form a detecting device, but after disassembly, they may each have their own purposes. In the present invention, after the absorbing element 201 is separated from the testing element, the absorbing element can be separately sterilized, such as sterilization by high temperature, X-ray, radiation, etc. After the sterilization, the absorbing element is combined with the testing element. By this way, the absorbing element can be brought into fluidic communication with the testing element such that the liquid from the absorbing element can flow from the absorbing element to the testing element. In some embodiments, the absorbing element 201 is fixedly disposed on the chamber 13 that accommodates the testing element, for example, on an end (as shown in FIG. 4); at this time, the testing element is not assembled on the chamber 13; after sterilization, the testing element 18 or the carrier 16 with the testing element is inserted into the chamber 13, and then fixed on the chamber 13 by a locking structure.

Testing Element

The "testing element" used herein refers to an element that can be used to detect whether a sample or a sample contains an interested analyte. Such testing can be based on any technical principles, such as immunology, chemistry, electricity, optics, molecular science, nucleic acids, physics, etc. The testing element can be a lateral flow test strip that can detect a variety of analytes. Of course, other suitable testing elements can also be used in the present invention.

Various testing elements can be combined for use in the present invention. One form of the testing elements is test paper or transverse-flow test paper. The test papers used for analyzing the analyte (such as drugs or metabolites that show physical conditions) in samples can be of various forms such as immunoassay or chemical analysis. The analysis mode of non-competition law or competition law can be adopted for test papers. A test paper generally contains a water absorbent material that has a sample application area, a reagent area and a testing area. Fluid or liquid samples are added to the sample application area and flow to the reagent area through capillary action. If analyte exists in the reagent area, samples will bind to the reagent. Then, samples continue to flow to the testing area. Other reagents such as molecules that specifically bind to analyte are fixed in the testing area. These reagents react with the analyte (if any) in the sample and bind to the analyte in this area, or bind to a reagent in the reagent area. Marker used to display the detection signal exists in the reagent area or the detached mark area.

Typical non-competition law analysis mode: if a sample contains analyte, a signal will be generated; and if not, no signal will be generated. Competition law: if no analyte exists in the sample, a signal will be generated; and if analyte exists, no signal will be generated.

The testing element can be a test paper, which can be water absorbent or non-absorbing materials. The test paper can contain several materials used for delivery of liquid samples. One material can cover the other material. For example, the filter paper covers the nitrocellulose membrane. One area of the test paper can be of one or more materials, and the other area uses one or more other different materials. The test paper can stick to a certain support or on a hard surface for improving the strength of holding the test paper.

Analyte is detected through the signal generating system. For example, one or more enzymes that specifically react with this analyte is or are used, and the above method of fixing the specifically bound substance on the test paper is used to fix the combination of one or more signal generating systems in the analyte testing area of the test paper. The substance that generates a signal can be in the sample application area, the reagent area or the testing area, or on the whole test paper, and one or more materials of the test paper can be filled with this substance. The solution containing a signifier is added onto the surface of the test paper, or one or more materials of the test paper is or are immersed in a signifier-containing solution; and the test paper containing the signifier solution is made dry.

Each area of the test paper can be arranged in the following way: sample application area, reagent area, testing area, control area, area determining whether the sample is adulterated, and liquid sample absorbing area. The control area is located behind the testing area. All areas can be arranged on a test paper that is only made of one material. Also, different areas may be made of different materials.

Each area can directly contact the liquid sample, or different areas are arranged according to the flow direction of liquid sample; and a tail end of each area is connected and overlapped with the front end of the other area. Materials used can be those with good water absorption such as filter papers, glass fibers or nitrocellulose membranes. The test paper can also be in the other forms.

The nitrocellulose membrane test strip is commonly used, that is, the testing area includes a nitrocellulose membrane (NC) on which a specific binding molecule is fixed to display the detecting result; and other test strips such as cellulose acetate membrane or nylon membrane test strips can also be used. For example, the test strips and similar apparatuses with test strips disclosed in the following patents can be applied to the testing elements or detecting devices in this invention for analyte detection, such as the detection of the analyte in the samples: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620, and 6,403,383. The test strips and similar device provided with a test strip disclosed in the above patent literatures may be applied in the testing element or detecting apparatus of the present invention for the detection of an analyte, for example, the detection of an analyte in a sample.

The test strips used in the present invention may be those what we commonly called lateral flow test strip, whose specific structure and detection principle are well known by those with ordinary skill in the art. Common test strip 18 (FIG. 9) includes a sample collecting area or a sample application area 183, a labeled area (182), a testing area 181 and a water absorbing area 184; the sample collecting area includes a sample receiving pad, the labeled area includes a labeled pad, the water absorbing area may include a water absorbing pad; where the testing area includes necessary chemical substances for detecting the presence or absence of analyte, such as immunoreagents or enzyme chemical reagents. The nitrocellulose membrane test strip is commonly used, that is, the testing area 181 includes a nitrocellulose membrane, and an area 1811 on which specific binding molecule is fixed to display the detecting result; and other test strips such as cellulose acetate membrane or nylon membrane test strips can also be used. Of course, in the downstream of the testing area, there may also be a detecting result control area 1812; generally, test strips appear on the control area and the testing area in the form of a horizontal line, that is a detection line or a control line, and such test strips are conventional. Of course, they can also be other types of test strips using capillary action for detection. In addition, there are often dry chemical reagent components on the test strip, for example immobilized antibody or other reagents. When the test strip meets liquid, the liquid flows along the test strip with the capillary action, and the dry reagent components are dissolved in the liquid, then the liquid flows to the next area, the dry reagents are treated and reacted for necessary detection. The liquid flow mainly relies on the capillary action. Here, all of them can be applied to the test device of the present invention or can be disposed in contact with the liquid samples in the detection chamber or used to detect the presence or absence of analyte in the liquid samples that enter the detection chamber, or the quantity thereof.

In addition to the foregoing test strip or lateral flow test strip which is used to contact with the liquid to test whether the liquid samples contain analytes, the testing element of the present invention may be used as a detecting device by itself to detect an analyte in a sample. Therefore, the detecting device here is equal to a testing element. For example, after being mixed with the treatment solution, the fluid sample is detected with a testing element directly. when the receiving device is described to treat a fluid sample, the testing element may be used for detection alone.

Analyte

Examples that can use the analyte related to this invention include small-molecule substance, including drugs (such as drug abuse). "Drug of Abuse" (DOA) refers to using a drug (playing a role of paralyzing the nerves usually) not directed to a medical purpose. Abuse of these drugs will lead to physical and mental damage, produce dependency, addiction and/or death. Examples of DOA include cocaine, amphetamine AMP (for example, Black Beauty, white amphetamine table, dextroamphetamine, dextroamphetamine tablet, and Beans); methylamphetamine MET (crank, methamphetamine, crystal, speed); barbiturate BAR (e.g., Valium, Roche Pharmaceuticals, Nutley, and New Jersey); sedative (namely, sleep adjuvants); lysergic acid diethylamide (LSD); depressor (downers, goofballs, barbs, blue devils, yellow jackets, methaqualone), tricyclic antidepressants (TCA, namely, imipramine, Amitryptyline and Doxepin); methylene dioxymetham-phetamine (MDMA); phencyclidine (PCP); tetrahydrocannabinol (THC, pot, dope, hash, weed, and the like). Opiates (namely, morphine MOP or, opium, cocaine COC; heroin, oxycodone hydrochloride); antianxietics and sedative hypnotics, antianxietics are drugs for alleviating anxiety, tension, fear, stabilizing emotion and having hypnosis and sedation, including benzodiazepines (BZO), non-typical BZs, fusion dinitrogen NB23Cs, benzoazepines, ligands of a BZ receptor, open-loop BZs, diphenylmethane derivatives, piperazine carboxylates, piperidine carboxylates, quinazoline ketones, thiazine and thiazole derivatives, other heterocyclic, imidazole sedatives/analgesics (e.g., oxycodone hydrochloride OXY, metadon MTD), propylene glycol derivatives, mephenesin carbamates, aliphatic compounds, anthracene derivatives, and the like. The detecting device of the present invention may be also used for detecting drugs which belong to medical use but is easy to be taken excessively, such as tricyclic antidepressants (Imipramine or analogues), acetaminophen and the like. These medicines will be resolved into micromolecular substances after being absorbed by human body, and these micromolecular substances will exist in blood, urine, saliva, sweat and other body fluids or in some of the body fluids.

For example, the analyte detected by the present invention includes but not limited to creatinine, bilirubin, nitrite, proteins (nonspecific), hormones (for example, human chorionic gonadotropin, progesterone, follicle-stimulating hormone, etc.), blood, leucocyte, sugar, heavy metals or toxins, bacterial substances (such as, proteins or carbohydrates against specific bacteria, for example, *Escherichia coli.* 0157: H7, *Staphylococcus, Salmonella, Fusiformis* genus, *Camyplobacter* genus, *L. monocytogenes, Vibrio*, or *Bacillus cereus*) and substances associated with physiological features in a urine sample, such as, pH and specific gravity. The chemical analysis of any other clinical urine may be conducted by means of a lateral cross-flow detection way and in combination with the device of the present invention. In some embodiments, the treatment solution contained in the receiving device is free of an analyte.

Detecting Device

The detecting device refers to an apparatus for detecting the presence or absence of an analyte. The collection device refers to a part that receives a part of the detecting device or a part that the detecting device inserted into the receiving device to mix or process the samples, elute the absorbing element 201 and treat the liquid or liquid samples. The receiving device is not present especially for receiving the detecting device, and may be present alone, and independently has the function of treating a fluid sample. The detecting device may include a testing element having a test function, for example, a carrier with a testing element, or may also include an accommodating element of a carrier, for example, a chamber 13 for accommodating the testing element. The detecting device may include an absorbing element 201 for collecting a sample, or include an absorbing element (a collector) with a connecting rod. The absorbing element 2022 with collected samples may be also called a collection device or a collector. The collection device may also include a detecting device; or the collector may be detachably combined with the detecting device. The collection device is assembled with the collection device in detection to complete the test. The detecting device may also include a collecting device. It is also possible that the collection device and the detecting device are an integrated structure, and once liquid samples are collected, the detection can be performed immediately to obtain the test result. Here, the connotation of the detecting device or testing element is interchangeable.

The "receiving device" here is merely for the convenience of description. In a detailed embodiment, the receiving device 14 receives a portion of the collector, for example, receives an absorbing element 2022, or receives a portion of the detecting device with an absorbing element. When the receiving device is not for the purpose of receiving, it may be called a sample treatment/sample mixing device. In the process of treating a sample, the detecting device may be not received, but the absorbing element may be only received to achieve independent completion (detailed description is as follows). To sum up, the "receive" here neither defines the scope of the device, nor play the defining role of claims of any Patent Law, but is merely a way of expression for the convenience of description.

In some detailed embodiments, the detecting device of the present invention includes a chamber 13 for accommodating the testing element; the testing element 18 has a first position and a second position in the chamber. When the testing element is located in the first position, the testing element is locked on or in the chamber 13. In some preferred embodiments, the detecting device includes a sliding element 11; the sliding element has a first position and a second position in the chamber 13, capable of moving to the second position from the first position. In some embodiments, when the sliding element is located in the first position, the sliding element is located in the locking position or locking state with the chamber 13; when or after being unlocked, the sliding element may move to the second position from the first position. In some embodiments, the testing element 11 may drive the testing element to move from the first position to the second position.

In some embodiments, the chamber for receiving the testing element has a three-dimensional structure as shown in FIGS. 4, 6-8. The chamber is used for receiving the testing element or bearing the carrier of the testing element. The carrier and chamber are in a locking state when in the first position, and may move to the second position from the first position when unlocked. In some embodiments, when the chamber is in the second position, a portion of the testing element contacts with a liquid sample to initiate the detection. In some embodiments, in case of being in the first position, the testing element is located in the chamber without exposure; in case of being in the second position, the testing element or a portion thereof stretches out of the chamber (FIG. 17), and the portion of the testing element stretching out of the chamber 13 contacts with the liquid sample. In some embodiments, the liquid sample is located in a chamber for treating liquid samples (a treatment chamber 14), for example, as shown in FIG. 1. The treatment chamber 14 contains a liquid sample; after the chamber 13 for accommodating the testing element is inserted into the treatment chamber 14, the testing element or the carrier bearing the testing element is unlocked from the locking state of the first position, thus moving from the first position to the second position. A portion of the testing element stretches into the treatment chamber 14 to contact with the liquid sample, thus completing the adsorption on the liquid sample.

Figure 6:
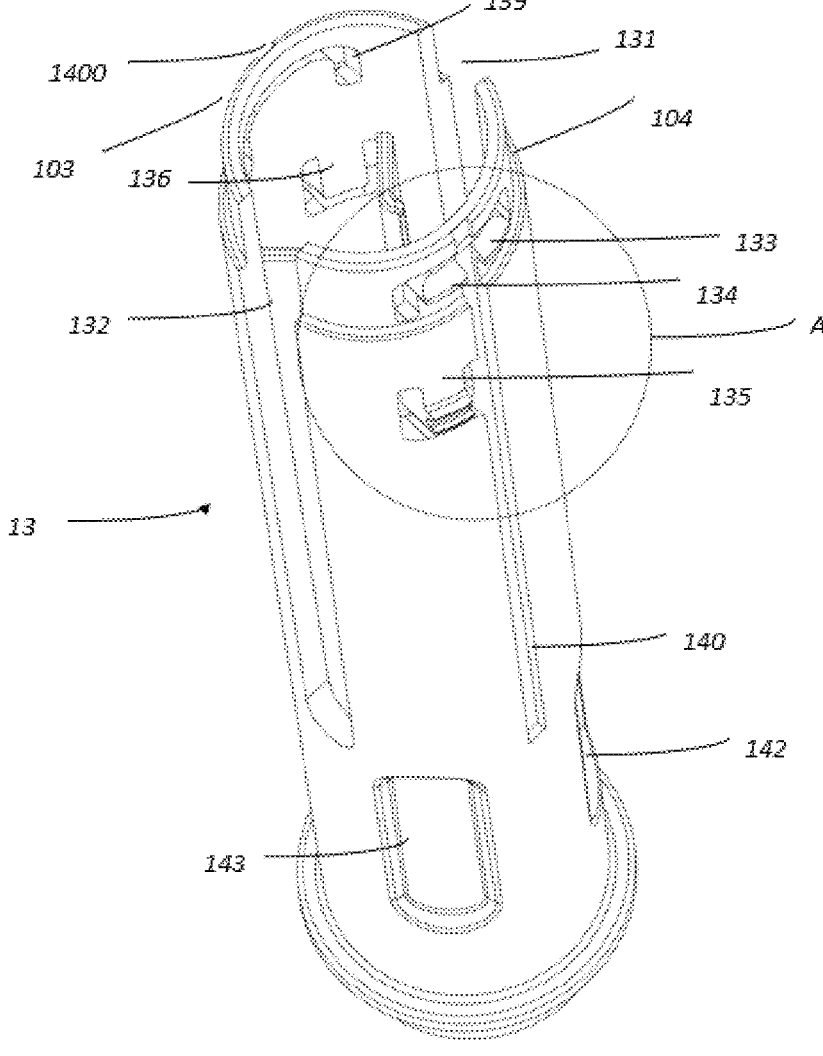
FIG. 6 is a schematic diagram showing a three-dimensional structure of a chamber for accommodating a carrier in a detailed embodiment of the present invention.
Figure 7:
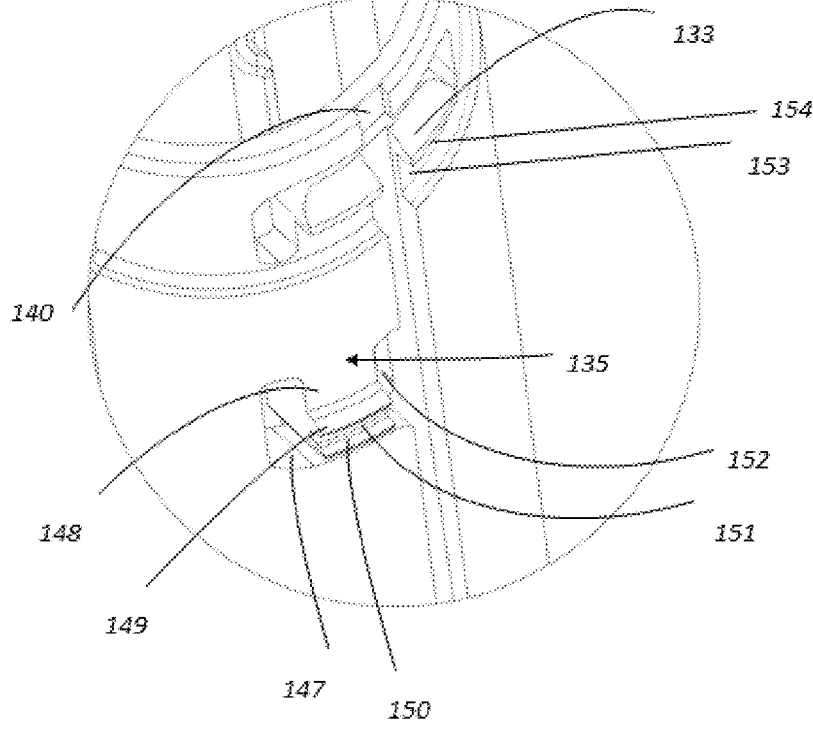
FIG. 7 is a structure diagram showing an expanded structure of the chamber for accommodating a carrier marked A in a detailed embodiment of the present invention.

It is understood that the testing element 18 or the carrier 16 bearing the testing element is located in two states or two position states in the chamber 13. In some embodiments, the chamber 13 is cylindrical; one end 103 is opened and another end 1032 is also opened; another end thereof has a structure which may be detachably assembled with the collector 201. The structure 156 may be an insertion hole 191; one end 2023 of the collector 201 may be inserted into the insertion hole 191, or fixed with the chamber 13 in threaded manner, thus being assembled into a collector. The collector has a rod-like body 2024 and an absorbing element 2022. In some embodiments, the locking state of the testing element or carrier or sliding element with the chamber is fixed on the chamber via a locking mechanism. The locking structure has locking and unlocking states; in case of being in the locking state, the position fixed on the chamber 13 may be fixed or not easy to move; in case of being in the unlocking state, the element fixed on the chamber may move or slide on the chamber. In some embodiments, the chamber includes a portion of locking structure, used for locking the testing element 18 or carrier 16 such that the testing element or carrier is in a locking state relative to the chamber 13. A portion of locking structure is shown in FIGS. 6-7; the portion of locking structure includes a sheet structure 135; the sheet structure is a portion of the side wall of the chamber, and has a notch 151; the notch includes upper and lower lugs, similar to a notch formed in the middle part of the two bulged plastic strips 149 and 150. Seen from the shape, the notch and the outer side wall of the chamber are located in the same position; and the two plastic strips 149,150 are slightly protruding on the outer side wall of the chamber. In some embodiments, the sheet structure is elastic. To make the structure with a notch elastic, the side wall of the chamber has two hollow structures 147,152 such that the sheet structure is similarly suspended on the side wall and the overall structure keeps a same plane with the side wall. In some embodiments, only one end is connected with the wall of the chamber 13. Other three sides of the sheet structure 135 are not connected with the chamber, forming a hollow structure. In this way, when the bulge structure 118 of the sliding element 11 passes through the sheet structure, the bulge structure is accommodated, matched, meshed or engaged with the notched structure such that the sliding element is locked on the chamber 13. When the bulge structure on the sliding element touches the sheet structure, but has not entered to the notched structure, the sheet structure will be bent towards the inside of the chamber slightly to generate deformation with movement. When the bulge 18 slides into the notch, elasticity disappears or the bulge springs back, the bulge structure is meshed with the notch, thereby completing a fixed state. In some embodiments, the sliding element 11 also has a chamber 1120 (FIGS. 12-13); a bulge structure 118 is disposed on the inner wall of the chamber; the bulge structure similar to a plastic rib is swelling on the inner wall of the sliding element. In some embodiments, a groove 116 is opened on the inner wall of the sliding element, and the groove has a bulge structure 118. Generally, the bulge structure is transversely parallel to the sliding element, and the notch on the outer wall of the chamber 13 is transverse, thus achieving the locking state between the sliding element 11 and the chamber when the sliding element moves from top to bottom. In some embodiments, the depth of the groove 116 is the height of the bulge structure 118; namely, only the bulge structure 118 is the highest relative to other parts of the groove.

Figure 12:
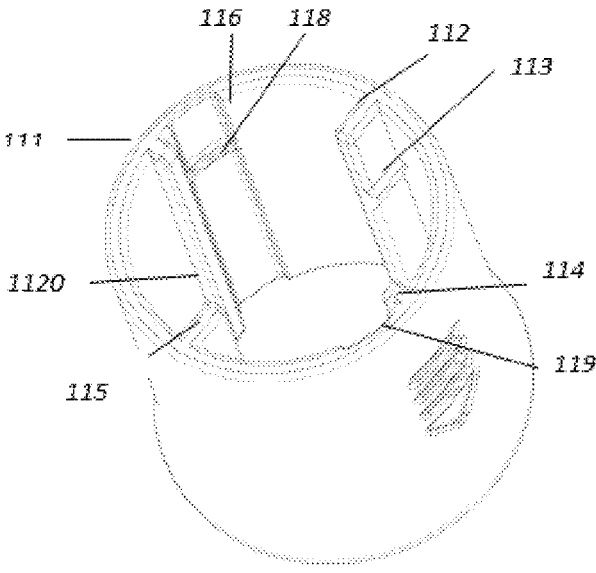
FIG. 12 is a schematic diagram showing a three-dimensional structure of a sliding element.
Figure 13:
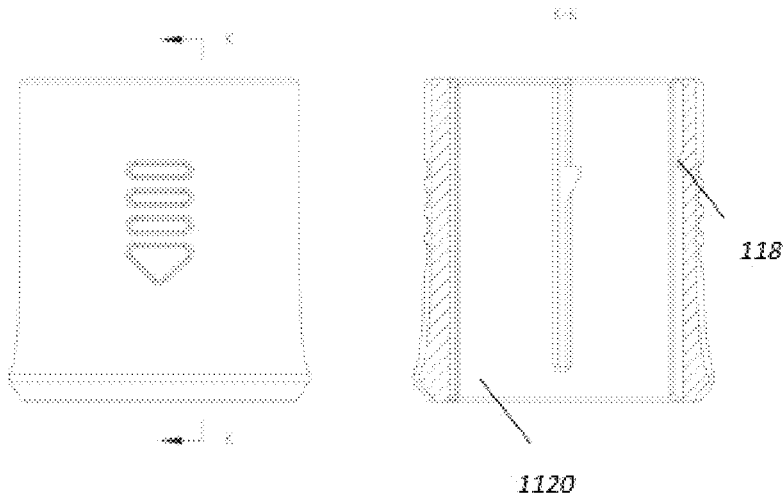
FIG. 13 shows a schematic diagram showing a sectional structure of the sliding element.

For example, on the sectional diagram of the sliding element as shown in FIGS. 12-13, the bulged plastic rib 118 is located nearby or close to the first sliding rail 111 and the third sliding rail 114 of the sliding element such that during sliding process, on the one hand, the sliding rail defines the route consistency of the sliding element from top to bottom, on the other hand, the sliding rail also defines the rotating performance of the sliding element, namely, the sliding element is basically not rotational but slides from top to bottom. In the case of not rotation like this, the bulge on the side wall of the sliding element may be matched with the notched element on the chamber 13, thus achieving the locking effect. Moreover, the height of the first sliding rail and/or second sliding rail protruding from the inner wall of the sliding element 11 is greater than the nearby bulge structure 118. The first sliding rail and third sliding rail in the sliding element 11 is in direct contact with the sliding groove 140 or/and 1400 on the outer wall of the chamber 13. Therefore, in some embodiments, the depth of the sliding groove outside the chamber 13 is smaller than the height of the sliding rail on the inner wall of the sliding element 11. In this way, when the sliding element 11 is sleeved on the chamber 13, there is an about 1-3 mm gap between the outer wall of the chamber and the inner wall of the sliding element 11 such that the outer wall of the chamber will be not in contact with the inner wall of the sliding element with large area. In this way, when the sliding element slides on the outer wall of the chamber 13, the sliding element may basically slide on the sliding groove via the sliding rail, thereby reducing frictional force and convenient for sliding. To achieve the height difference between the sliding groove 140 on the outer surface of the chamber and the sliding rail 111 inside the movable element, one of the optimal ways is that the sliding groove has a bottom surface, thus achieving the height difference and reducing frictional force, which is substantively different from the other sliding rails 131,132 of the chamber and specifically described below.

Moreover, the notch 151 on the outer surface of the chamber is formed by upper and lower protruding strips 149,150. When the protruding strips are higher than the outer surface of the chamber 13, there is a certain width of gap between the inner surface of the sliding element 11 and the outer surface of the chamber 13, and the two protruding strips 149,150 will not substantively contact the inner surface of the movable element 11, thus reducing the resistance of the movable element sleeved on the outer surface of the chamber 11. When the movable element 11 slides to the position of the notch 151, the protruding strip 118 located in the movable element 11 is easy to be meshed and clamped by the notch 151. Certainly, what is described above is merely an embodiment of the locking structure. In some embodiments, one protruding strip 149 may be disposed on the sheet structure 135 on the outer surface of the chamber 13 only without a notch 151 and other protruding strip 150, thus achieving the locking between the sliding element and the chamber. The protruding strip 118 in the groove 116 nearby the sliding rail 111 of the sliding element is still constant. When the sliding element 11 is sleeved on the outer surface of the chamber 13, the protruding strip 118 of the movable element 11 is touched by the protruding strip 149 of the sheet structure 135 on the outer surface of the chamber 13 to block the further sliding of the movable element, which also achieves the locking state between the movable element 11 and the chamber 13. The locking here means that the movable element 11 is fixed in the position of the chamber 13 under different states. The movable element 11 may not continue to move up and down on the chamber 13, but be located in a fixed position here. Therefore, in some embodiments, the sliding element is locked in a certain fixed position on the chamber 13 for accommodating the testing element, which may be called a first position or a first initial position here. The sliding element 11 is very light by itself. After being provided with the testing element or a carrier for bearing the testing element, it is still lighter in some embodiments. Therefore, the notch 151 and the protruding rib strip 118 may be designed simply as long as buckling can be achieved. In some embodiments, the sheet notched structure is located nearby the sliding groove 140 with a bottom surface of the chamber and close to the upper end of the chamber. Certainly, there are other possible locking structures except the above locking structure, for example, a bolt, a jack, clamping and the like. In terms of simple design, the locking structure described in detail herein can be achieved most easily and conveniently.

Figure 8:
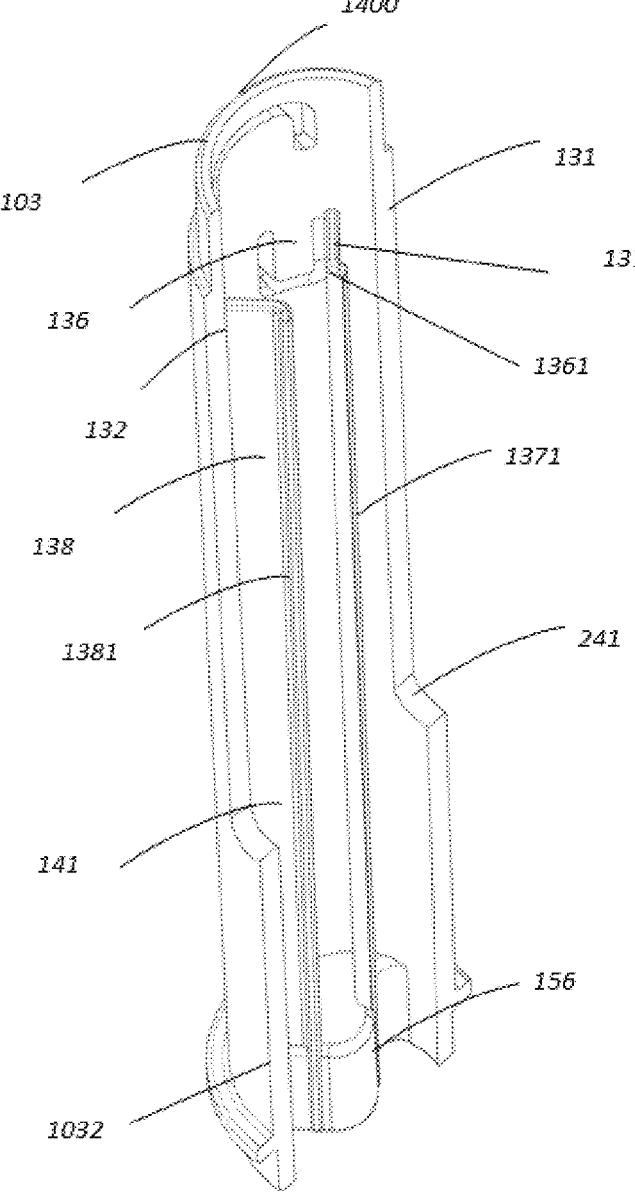
FIG. 8 is a schematic diagram showing a portion of the sectional structure of the chamber for accommodating a carrier in a detailed embodiment of the present invention.

In some embodiments, the chamber for accommodating the testing element is divided into two parts 103,104 by symmetrical sliding grooves 132,131. The length of the sliding grooves limits the sliding distance of the sliding element 11 on the chamber 13. Moreover, the sliding distance of the sliding element is also limited by the sliding groove 140 with a bottom surface of the chamber 13. For example, as shown in FIG. 8, a function of the sliding grooves 132,131 penetrating through the side wall is to guide the sliding track and distance of the sliding rails 112,115 on the sliding element 11. Another important function is as follows: when there is a carrier element 16, and the sliding element 11 drives the carrier element 16 to slide together, the state of the carrier element in the chamber may be identified clearly. Meanwhile, when the sliding element is located in the first position, a portion of the carrier is located in the chamber 13 and the gap of the sliding grooves 132,131 is filled up by the portion of the carrier, which still appears an integral structure. In some embodiments, the carrier is fixedly connected with the sliding element. The specific connecting way will be described in detail below. Therefore, a function of the sliding rails 112,115 separately disposed on the movable element 11 is to allow sliding on the chamber, and another important function is to connect the carrier with the movable element. The movable element 11 drives the carrier 16 to move from the first position to the second position during sliding process. Moreover, the two sliding rails 131,132 penetrating through the side wall which are opened on the chamber 13 are to reduce the contact with the carrier, thus reducing the frictional force between the chamber 13 and the carrier, which is convenient for the carrier 16 to slide or move freely in the chamber to reduce the frictional force. This is another advantage or function of the sliding rails 131,132 penetrating through the side wall 13. A large inner diameter of the chamber 13 may be designed, but to achieve a compact test device and convenient operation, the lateral dimension of the carrier 16 should keep best adaptability to the size of the chamber 13 basically. If the whole test device has a very large size, it is not easy to operate. For the purpose of a compact design, it is inevitable to solve some inherent problems of a compact structure, for example, the problem of frictional force, a locking function needs to be demanded. A structure is expected to move easily to reduce resistance when the structure is required to move internally. Therefore, one of the above designs may solve these functional demands.

Carrier Element

Figure 9:
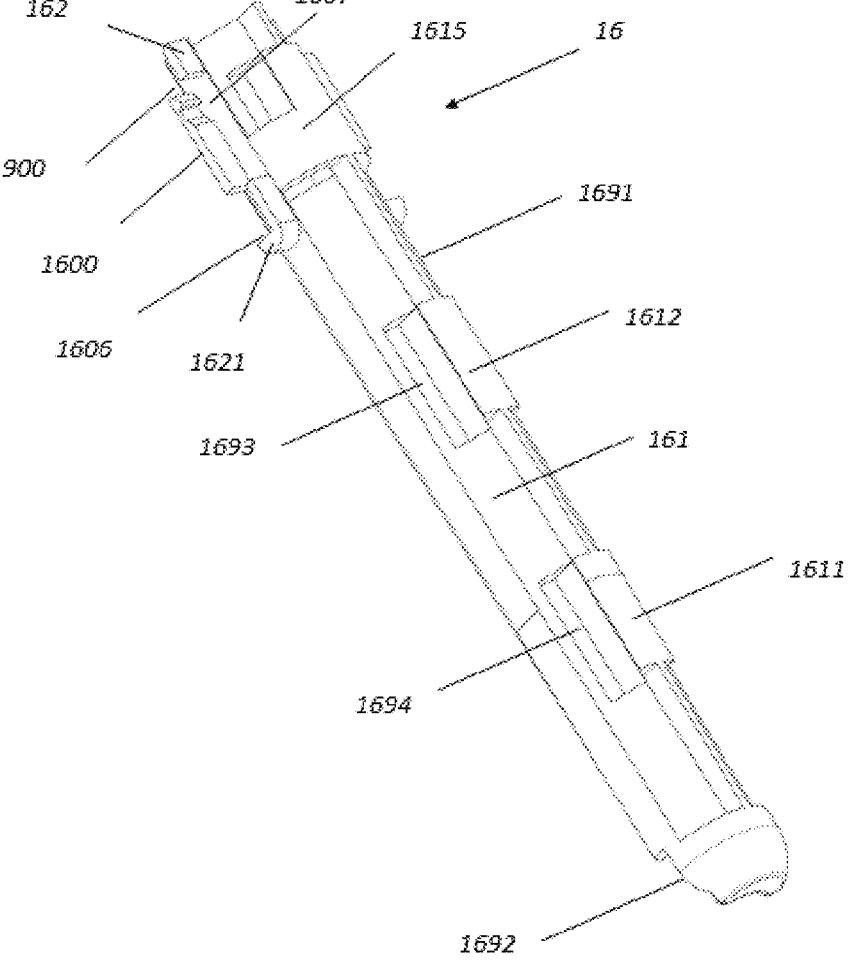
FIG. 9 is a structure diagram showing a carrier in a detailed embodiment of the present invention.
Figure 11:
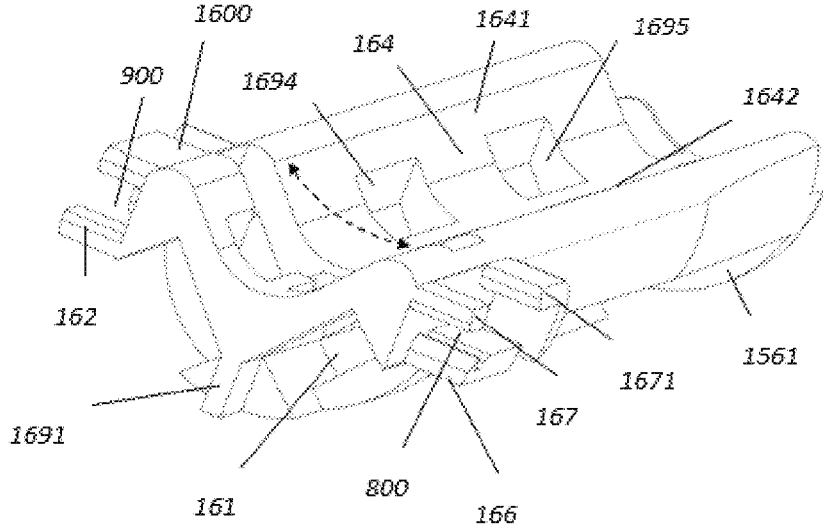
FIG. 11 is a schematic diagram showing a carrier structure in a detailed embodiment of the present invention.

In some detailed embodiments, the testing element may be also disposed on some carrier elements; then the carrier elements contain the testing element to complete the detection and assay of the analytes in fluid samples. Therefore, in some embodiments, the detecting device includes a carrier 16, and the carrier is provided with a testing element 18. In some embodiments, the carrier is located in the chamber 13 for accommodating the testing element, and the carrier has a first locking position and a second position in the chamber; and the second position is not a locking state. As shown in FIGS. 9-11, for example, on some carrier 16, generally, a carrier has one or more grooves 1617; the testing element 18 is located in the groove 161, and the carrier generally has a front and a back 164, and the testing element 18 is located on the front of the carrier, or located in the front groove 161. The number of grooves is not limited; generally, a testing element is located in a groove; usually, a testing element may be used to detect an analyte in samples. Of course, a testing element may be used to simultaneously detect one or more, a or a plurality of analytes.

In some detailed embodiments, the carrier 16 includes two parts, and one of them is a groove structure 161; the groove structure is used for holding a testing element; generally, the groove structure is used for holding the testing area or labeled area of the testing element such that the testing area or the labeled area is located in a relatively fixed and safe position. Such a design may ensure the accuracy and reliability of the test results. The carrier further includes an area connected to the sliding element 11. The structure of the area is designed in fixed fit with the sliding element. In some embodiments, when the chamber for accommodating the testing element is round, the carrier is designed in a curved surface. Therefore, the groove for accommodating the testing element on the carrier is distributed according to a curved surface. Specifically, the carrier shows a regular curved surface on the whole. The middle part of the curved surface has a backbone 1691; the carrier is divided into two parts by the backbone 1691; each part is provided with a groove for accommodating a reagent strip; the testing element is located in the groove 161. The backbone is provided with horizontal extension areas 1612,1611; the extension areas are distributed above the groove on the backbone. In this way, when the testing element 18 is disposed in the groove, the extension areas may protect the test stripe from being damaged. The major reason is that the carrier is driven to move in the chamber 13; during the moving process, it needs to ensure the testing element free of damage, and also needs to ensure a fixed position of the testing element in the groove. Otherwise, the location change of the testing element will also affect the accuracy of the final test result. For example, household operation has high arbitrariness because the operator does not possess enough professional knowledge, which demands for the fixed position of each component and for the convenience of the operation.

Moreover, to keep the position of the testing element in the groove still and not separated from the groove, a tail end of the carrier is provided with a blocking piece 1692 (FIG. 9). The blocking piece has a plane 1561 (FIG. 10) in contact with the tail end of the testing element, thus preventing the test stripe from falling off from the groove. In the subsequent movement, the carrier needs to stretch out of the chamber 13, and the stretched portion needs to be immersed into liquid. The testing element is not desired to slip out of the groove. Meanwhile, the tail end of the carrier has a cyclic structure 1698 which half-wraps the tail end of the test stripe. The major function of the cyclic structure is to protect the tail end of the test stripe. Because when the carrier 16 drives the test stripe 18 to stretch out of one end of the chamber, the stretched portion is inserted into the chamber 104 of an accommodating chamber 14 and contact with a liquid sample. At this time, a collector is located in the chamber 104 of the accommodating chamber such that the testing element is not damaged and the tail end of the test stripe is always protected. In some other examples, through holes 1693,1694,1695 are opened in the groove and distributed in the different positions of the groove. It needs to be indicated that one of the through hole is disposed on the plane 1561 of a stopper 1692 to be communicated with the plane. When the tail end of the testing element touches the surface 1561 of the stopper, a portion of testing element is exposed through the through hole 1695, in particular to the sample application area of the partial testing element is exposed. In this way, when the carrier stretches out of the chamber 13 and enters to the chamber of a collection device, the carrier will directly touch the liquid sample in the chamber of the collection device; the sample contacts with the sample application area of the testing element after passing through the through hole 1695. Another through hole 1694 is disposed in a roughly middle position of the groove to prevent the liquid sample from wetting the test stripe in advance after passing through the capillary gap formed between the back of the testing element and bottom surface of the groove, thus affecting the normal reaction. The through hole plays the role of blocking. Generally, the liquid flow rate by the capillary force of the test stripe is much slower than the liquid flow rate of the capillary gap. In this way, if other areas of the testing element are moistened in advance, for example, a testing area, the may not be completed when the liquid sample carrying analyte flows to the testing area. Because the testing area is moistened by the liquid in advance, the area is free of capillary force, thus affecting the flow of the liquid sample.

Figure 14:
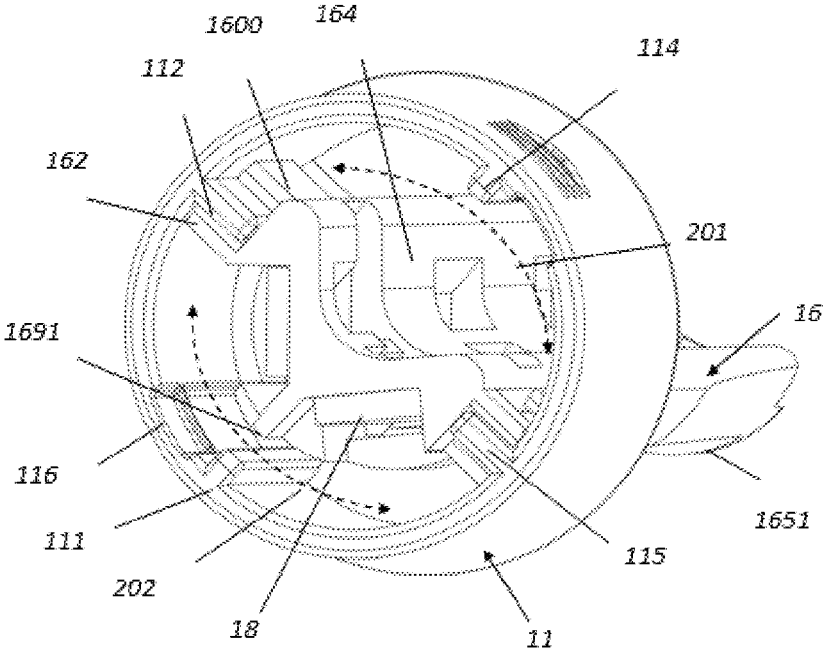
FIG. 14 shows a schematic diagram showing a structure that the sliding element is connected to the carrier.
Figure 15:
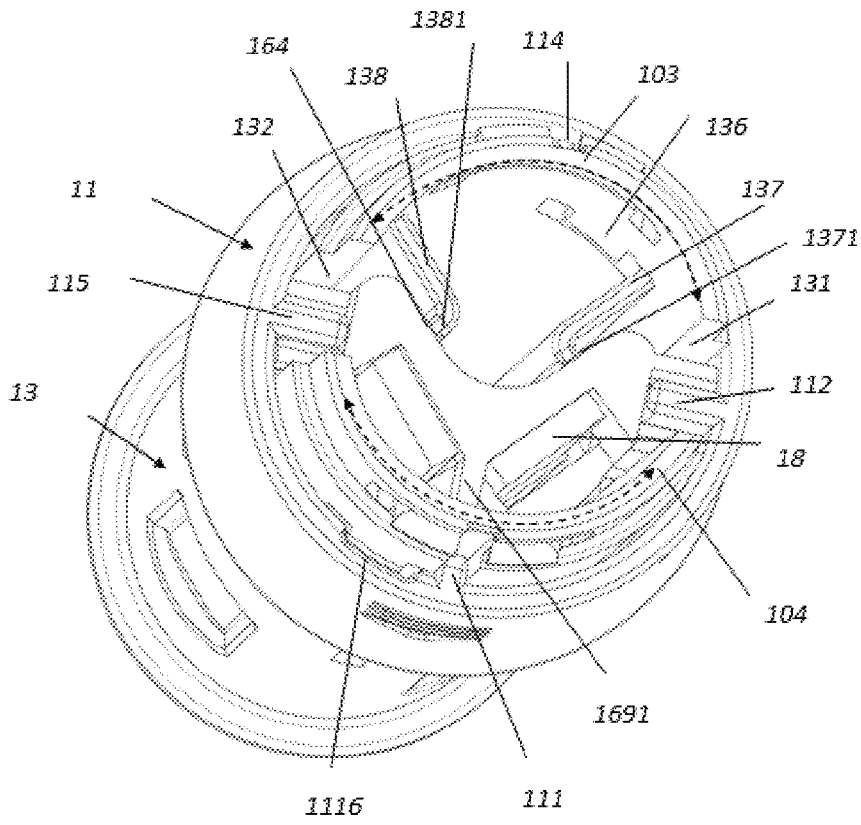
FIG. 15 shows a schematic diagram showing columnar structures of the sliding element, carrier and chamber.
Figure 16:
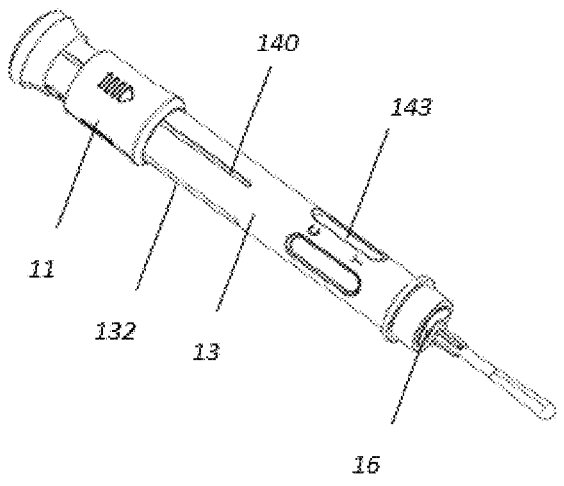
FIG. 16 shows a structure diagram that the sliding element is located in a first locking position in a detailed embodiment of the present invention.

In some embodiments, a structure fixed with the movable element 11 is disposed on another end of the carrier, namely, one end close to the water absorbing area 184 of the testing element. The carrier is connected with the movable element by the structure. In this way, the movable element moves to drive the carrier to move. The carrier may not only drive the testing element to move, but also protect the testing element from being damaged. In some embodiments, the sliding element 11 is also a hollow structure having an internal space 1120. Side wall of the inner part of the hollow structure has a second sliding rail 112 and a fourth sliding rail 115. The first function of the sliding rail is to set in the sliding grooves 132,131 of the chamber 11, thus driving the carrier to slide in the chamber. Another function is to connect the carrier with the sliding element. The sliding rail 112 and fourth sliding rail 115 are distributed symmetrically protruding from the hollow side wall to the central position has a certain width (FIG. 10), and the carrier 16 is provided with a suspending structure. The carrier is connected with the sliding rails of the movable element by the suspending structure. Specifically, the suspending structure includes three staggered strip structures 167,166,1671 (as shown in FIGS. 11, 9). The first strip structure 166 and the second strip structure 167 are distributed on the tail end of the carrier, and there is a gap 800 or a preset distance between the two strip structures. The width of the gap is matched with the fourth sliding rail 115 of the sliding element such that the fourth sliding rail 115 is inserted into the gap. The third strip structure 1671 is located below the first and second strip structures, being an L shape and having a plane. During assembly, the suspending structure of the carrier moves upward from the inner space of the sliding element such that the fourth sliding rail 115 is inserted into the suspending structure via the gap 800. The third strip structure 1671 is L-shaped to define the insertion depth of the second sliding rail in the gap 800. Specifically, similar suspending structures are respectively disposed at both sides of the carrier. Specifically, the suspending structure includes three staggered strip structures 162,1600,1621 (as shown in FIGS. 11, 9). The first strip structure 162 and the second strip structure 1600 are distributed on the tail end of the carrier, and there is a gap 900 between the two strip structures. The width of the gap is matched with the second sliding rail 112. The third strip structure 1621 is located below the first and second strip structures, being an L shape; the third strip structure has a plane 1606 to define the insertion depth of the second sliding rail 112. During assembly, the suspending structure of the carrier moves upward from the inner space of the sliding element such that the second sliding rail 112 is inserted into the suspending structure via the gap 900. The third strip structure 1671 is L-shaped to define the insertion depth of the second sliding rail in the gap 900. The structure formed after the sliding element is assembled with the carrier is shown in FIG. 15. At this time, the backbone structure 1691 of the carrier faces the third sliding rail 111; the face 164 with a sunk curved surface faces the first sliding rail 114 facing the third sliding rail. At this time, there is a certain distance between the third sliding rail 111 and the backbone structure 1691 (FIG. 14: 202 as shown in the bent double-headed arrow). There is also a certain distance between the face 164 with a sunk curved surface and the first sliding rail 114 (FIG. 14: 201 as shown in the bent double-headed arrow). The carrier is similarly suspended in the central position of the hollow sliding element 11, and the second sliding rail is connected with the fourth sliding rail through the sliding rail of the sliding element. Others are not in contact with the inner wall of the hollow sliding element. These distances are configured as follows: when the side wall of the chamber 13 needs to pass through these preset distances to be sleeved with the sliding element, the movable element 11 may drive the carrier element to move in the chamber 13. Since the carrier and the movable element 11 are connected with each other via the sliding rails 112,115, the sliding rails 115 and 112 on the chamber 13 are penetrated (131,132) with the sliding groove, which is different from the design of another sliding groove 140 on the chamber. Otherwise, the carrier may not be driven to move in the chamber 13. At this time, the sliding element is disposed outside the outer wall of the chamber 13. Two different forms of sliding rails are matched with the different forms of sliding grooves on the chamber 13. The carrier is connected with the sliding element 11 to be designed in the chamber 13, thus driving the movable element 11 to move relying on the outside such that the carrier moves in the chamber 13. It needs to be indicated herein that in the above detailed embodiments, two pairs of sliding rails are set on the movable element. It can be understood that even though any pair of sliding rails may be shortage, the movable element 11 may still drive the testing element 18 or a carrier element 16 to move from the first locking position to the second position in the chamber 13.

When the sliding element with a carrier element is assembled on the chamber 13, for example, as shown in FIG. 15, the chamber 13 has an opened sliding groove 132,131; the chamber is divided into two parts 103,104 by the sliding groove. Meanwhile, a limiting structure is disposed in a portion of the chamber; the limiting structure allows the carrier to enter into the chamber 13 only through a direction. Specifically, the limiting structure is similar to two symmetrically configured wing-like sheet structures 138,137. The two sheet structures are closed up on the edges 1381, 1371 to be an "eight" shape integrally, and extend to the central position of the chamber from the inner wall of the chamber 13. When the product needs to be assembled, the movable element with a carrier is inserted from one end of the chamber 13; the insertion direction is that the concaved curved surface of the carrier touches the limiting structures 137,137 and contacts with the edges 1371,1381 of the limiting structure, thus sliding into the chamber 13. On the one hand, the function of the limiting structure is to define the entry direction of the carrier; the concaved curved surface of the carrier only enters to the chamber 13 relying on the edges of the limiting structure. Moreover, the contact between the edges of the limiting structure and the surface of the concaved curved surface also plays the role of guiding the movement of the carrier. At this time, when the second sliding rail 112 and the fourth sliding rail 115 respectively enter to the sliding grooves 131,132 of the chamber, edges 1371,1381 of the wing-like sheet structures 138,137 touch the concave side of the curved surface carrier, and the side wall 131 of partial chamber 13 will pass through the space between the concave side 164 of the curved surface and the side wall of the chamber of the sliding element 11. The side wall 104 of partial chamber 13 will pass through the gap between the third sliding rail 111 of the sliding element and the backbone structure 1691 of the curved surface carrier. In this way, the third sliding rail 111 and first sliding rail 114 located in the sliding element are matched with the sliding grooves 140 and 1400 on the outer wall surface of the chamber 11. When the movable element 11 moves on the outer surface of the chamber 13, the sliding position of the carrier in the chamber 13 is always kept longitudinally consistent to achieve stable direction and route by relying on the sliding rails on the movable element 11 and sliding groove of the chamber 13, edges of the limiting structure. In this way, a portion of the side wall 103 of the chamber 13 for accommodating the carrier is located between the concave side 164 of the carrier 16 and the side wall of the sliding element (as shown in double-headed arrow). Another portion of the side wall 104 of the chamber 13 for accommodating the carrier is located between the backbone structure 1691 of the carrier 16 and another side wall of the sliding element.

For example, FIG. 15 shows a three-dimensional structure diagram that the sliding element is mounted at one end of the chamber 11 and located in the locking position. It can be seen from FIG. 15 that when the concave side 164 of the curved surface is not in contact with the edges of the wing-like sheet structures 138,137, but changes in direction, and the backbone structure 1691 of the curved surface carrier faces the wing-like sheet structures, the carrier 16 may not enter into the chamber 13 correctly. This configuration is for the purpose of assembly and free of error. This configuration will form a more compact structure, and meanwhile, the movement of the carrier in the chamber 13 will be not disturbed or obstructed.

During assembly, the bulge structure located nearby the first sliding rail is matched with the notched structure on the chamber such that the sliding element is located on the chamber 13. At this time, the carrier and the testing element on the carrier are indirectly locked on the relatively fixed position of the chamber. At this time, the whole carrier and the test stripe on the carrier are surrounded by the chamber 13. Only a collector is exposed outside the detecting device such that the operator spontaneously envisages collecting a sample with the collector upon seeing such a structure. After collecting the sample, the collector is inserted into the chamber of the accommodating device 14. At this time, the accommodating device vertically stands on the table. Inner wall of the opening of the accommodating device is matched with the outer edge 109 at another end of the chamber 13 such that the outer edge 109 is inserted into the opening of the accommodating chamber; on the one hand, the opening is sealed to avoid the leakage of the liquid sample during operation. For example, the collecting element 2022 of a collector is used to absorb saliva, urine, sputum or nasal secretion, and then inserted into an accommodating device 14. At this time, the opening is sealed by the outer edge 109. At this time, the movable element is located in the first locking position, and the testing element 18 of the carrier is located in the chamber 13. When test needs to be done, the movable element is located in the unlocking state, and then the movable element moves to the second position from the first position. Such a motion is specifically as follows: the carrier is driven by the motion of the sliding rail on the movable element and the sliding groove on the chamber 13 to move such that a portion of the carrier stretches out of the chamber 13. The stretched portion also enters to the chamber of the accommodating device 14. In this way, a portion of the sample application area of the testing element contacts the liquid sample. The liquid sample flows from the upstream of the testing element to the downstream labeled area relying on the capillary action generated by the water absorption of the testing element. Accordingly, the testing area completes the detection or assay of the analyte in the sample. At this time, due to the movement of the position, the testing area of the testing element is located below the window 143 for reading the test result on the chamber 13, which may read the test result on the testing area. After reading the test result, the whole detecting device may be discarded directly. The accommodating device 14 includes an accommodating chamber 141 which accommodates a collector and a portion of carrier. Moreover, there are two supporting walls 143,142 such that the accommodating device stands on the table firmly.

Cover Body Structure

Figure 5:
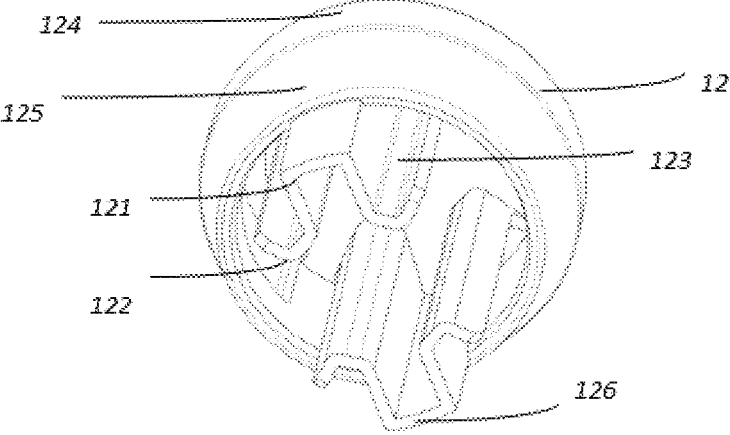
FIG. 5 is a structure diagram showing a cover body in a detailed embodiment of the present invention.
Figure 18:
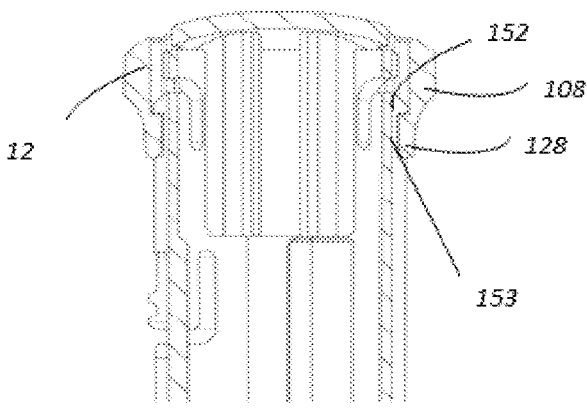
FIG. 18 is a schematic diagram showing a sectional structure that a cover body covers an opening of the chamber in another embodiment of the present invention.

As shown in FIGS. 5 and 18, in some embodiments, the detecting device of the present invention further includes a cover body element 12. The cover body element is matched with an opening at one end of the chamber 13. The opening of the end is used for sleeving the movable element 11. The cover body includes a cover main body 124 and a cover extension portion 125; the cover body has sliding rails disposed symmetrically. The sliding rail is matched with the sliding grooves 131,132 of the chamber and located in the chamber 13. In this way, the cover body may be stably inserted into one end of the opening of the chamber 13. One end of the opening of the chamber is in a sealed state. The sliding rail of the cover body has a hollow pipeline chamber 121 and elastic wing-like compression pieces 122,123 distributed at both sides. When the cover body is inserted into the opening of the chamber 13, the elastic compression pieces will touch the inner wall of the chamber 13 such that the cover body does not easily drop off. To achieve more firm fixation of the cover body on the chamber 13, one end of the opening of the chamber 13 is provided with one or more suspending structures. The suspending structure is similar to a hook structure. As shown in FIG. 7, the suspending structure 133 includes a hook body 154 and a hook handle 153. These structures may be designed in pairs, for example, the structures 133,134 as shown in FIG. 7. These structures are basically a portion of the side wall of the chamber. The cover body has a hook structure matched with a suspending hook, for example, a portion of the cover edge 108 and a platform structure 128 as shown in FIG. 19; when the cover body 12 covers on the chamber 13, the inner sliding rail is inserted into the sliding groove; the suspending hook on the outer surface of the chamber 13 is matched with the corresponding structure of the cover body such that the cover body is fixed on one end of the opening of the chamber 13 more firmly.

All patents and publications mentioned in the description of the present invention are disclosures of the prior art and they may be used in the present invention. All patents and publications referred to herein are incorporated in the references as if each individual publication is specifically referred to separately. The invention described herein may be practiced in the absence of any one or more of the elements, any one limitation or more limitations that are not specifically recited herein. For example, the terms "comprising", "consisting of . . . substantively" and "consisting of . . . " in each example herein may be replaced by the rest 2 terms. The so-called "a/an" herein merely means "one", but does not exclude including 2 or more instead of including only one. The terms and expressions which have been employed herein are descriptive rather than restrictive, and there is no intention to suggest that these terms and expressions in this description exclude any equivalents, but it is to be understood that any appropriate changes or modifications can be made within the scope of the present invention and appended claims. It should be understood that, the embodiments described in the present invention are some preferred embodiments and features, and any person skilled in the art may make some changes and variations based on the essence of the description of the present invention, and these changes and variations are also considered to fall into the scope of the present invention and the independent claims and the appended claims.

The invention claimed is:

1. A device for detecting an analyte in a fluid sample comprising:
a chamber for receiving a testing element, wherein the testing element has a first position and a second position in the chamber;
the testing element is not in contact with the fluid sample when the testing element is located in the first position; and the testing element is in contact with the fluid sample when the testing element is located in the second position;
wherein the chamber further comprises a carrier used for bearing the testing element; the carrier has a first position and a second position in the chamber; and the carrier drives the testing element to change or move between the first position and the second position, or the carrier drives the testing element to move from the first position to the second position;
wherein the device further comprises a movable element; the movable element is connected with the carrier; and the movable element is capable enabling the carrier to move from the first position to the second position; and
wherein the movable element comprises a first sliding rail and a second sliding rail; the carrier is fixedly connected with the second sliding rail.

2. The device according to claim 1, wherein the chamber is further connected with a fluid sample collector, and the fluid sample collector is disposed on one end of the chamber.

3. The device according to claim 2, wherein the device further comprises an accommodating device; the accommodating device is used for accommodating the collector and a portion of the testing element.

4. The device according to claim 3, wherein the portion of the testing element comprises a portion of a sample application area.

5. The device according to claim 1, wherein the testing element and the chamber are in a locking state when the testing element is located in the first position.

6. The device according to claim 1, wherein a portion of the testing element stretches out of the chamber when the testing element is located in the second position.

7. The device according to claim 1, wherein the carrier is connected to the chamber by a locking structure; the carrier does not move with respect to the chamber when the carrier is in a locking first position, or, the carrier is capable of moving to the second position from the first position relative to the chamber when the locking structure is unlocked.

8. The device according to claim 7, wherein when the carrier is located in the first position, the whole carrier is completely located in the chamber; when the carrier is located in the second position, a portion of the carrier stretches out of the chamber, thus contacting the fluid sample.

9. The device according to claim 1, wherein the chamber comprises a first sliding groove matched with the first sliding rail of the movable element and a second sliding groove matched with the second sliding rail of the movable element; the second sliding groove penetrates through a side wall of the chamber, and the first sliding groove is located on an outer surface of the chamber.

10. The device according to claim 9, wherein the movable element is sleeved on an outer surface of the chamber, and the carrier and the second sliding rail are located in the chamber for receiving the testing element; the first sliding rail is located on the outer surface of the chamber and matched with the first sliding groove on the surface of the chamber.

11. The device according to claim 10, wherein the chamber comprises a limiting structure; the limiting structure comprises an edge; the carrier is a curved surface structure; a concave surface of the carrier is in contact with the edge of the limiting structure, wherein the carrier comprises a backbone structure.

12. The device according to claim 11, wherein the chamber for receiving the testing element comprises a first chamber side wall and a second chamber side wall, wherein the first chamber side wall faces the concave surface of the carrier, and the second chamber side wall faces the backbone structure.

13. The device according to claim 1, wherein the movable element comprises a portion of the locking structure, and the chamber comprises another portion of the locking structure; the movable element is fixed on the chamber via the locking structure.

14. The device according to claim 13, wherein the locking structure comprises a bulge structure and a notched structure; the movable element comprises the bulge structure; and an outer wall of the chamber comprises a notched structure.

15. The device according to claim 14, wherein the notched structure is located at a sheet structure on a side wall of the chamber; the sheet structure is a portion of the side wall of the chamber; meanwhile, the sheet structure is elastic.

16. The device according to claim 1, wherein the carrier comprises a suspending structure, and the carrier is fixedly connected on the second sliding rail via the suspending structure.

17. The device according to claim 1, wherein the fluid sample is saliva, sputum, urine or nasal secretion; and the analyte comprises corona virus.

\* \* \* \* \*